United States Patent [19]

Matsushita et al.

[11] Patent Number: 4,761,075
[45] Date of Patent: Aug. 2, 1988

[54] CELLULAR ANALYSIS SYSTEM

[75] Inventors: Hajime Matsushita; Ryohei Yabe, both of Katsuta; Masaaki Kurimura, Ibaraki; Toshiaki Yokobayashi, Katsuta, all of Japan

[73] Assignee: Hitachi, Ltd., Tokyo, Japan

[21] Appl. No.: 938,964

[22] Filed: Dec. 8, 1986

[30] Foreign Application Priority Data

Dec. 10, 1985 [JP] Japan ............................ 60-277719

[51] Int. Cl.$^4$ .......................................... G01N 33/48
[52] U.S. Cl. ...................................... 356/39; 356/394; 356/432
[58] Field of Search ..................... 356/39, 72, 73, 432, 356/394; 414/331; 350/529

[56] References Cited

U.S. PATENT DOCUMENTS

| 3,851,972 | 12/1974 | Smith et al. | 356/39 X |
| 3,906,120 | 9/1975 | Geating | 427/4 |
| 4,225,229 | 9/1980 | Gohde | 356/39 |
| 4,513,438 | 4/1985 | Graham et al. | 382/6 |

Primary Examiner—Eugene R. LaRoche
Assistant Examiner—Robert J. Pascal
Attorney, Agent, or Firm—Antonelli, Terry & Wands

[57] ABSTRACT

An automatic cell analyzing system for automatically analyzing a large number of sample slides prepared for cellular samples. The sample slides include a plurality of sample slide sets each prepared by different staining methods for each sample. Cellular images obtained by observing through a microscope the numerous sample slides picked out sequentially are analyzed by an image fetching/feature extracting circuit, the resulting morphological features of the individual cells being converted into digital information to be stored. Upon completion of the analysis for all the sample slides, the digital information obtained from the sample slide is synthetically examined for each associated sample to thereby classify the sample into one of predetermined categories.

6 Claims, 4 Drawing Sheets

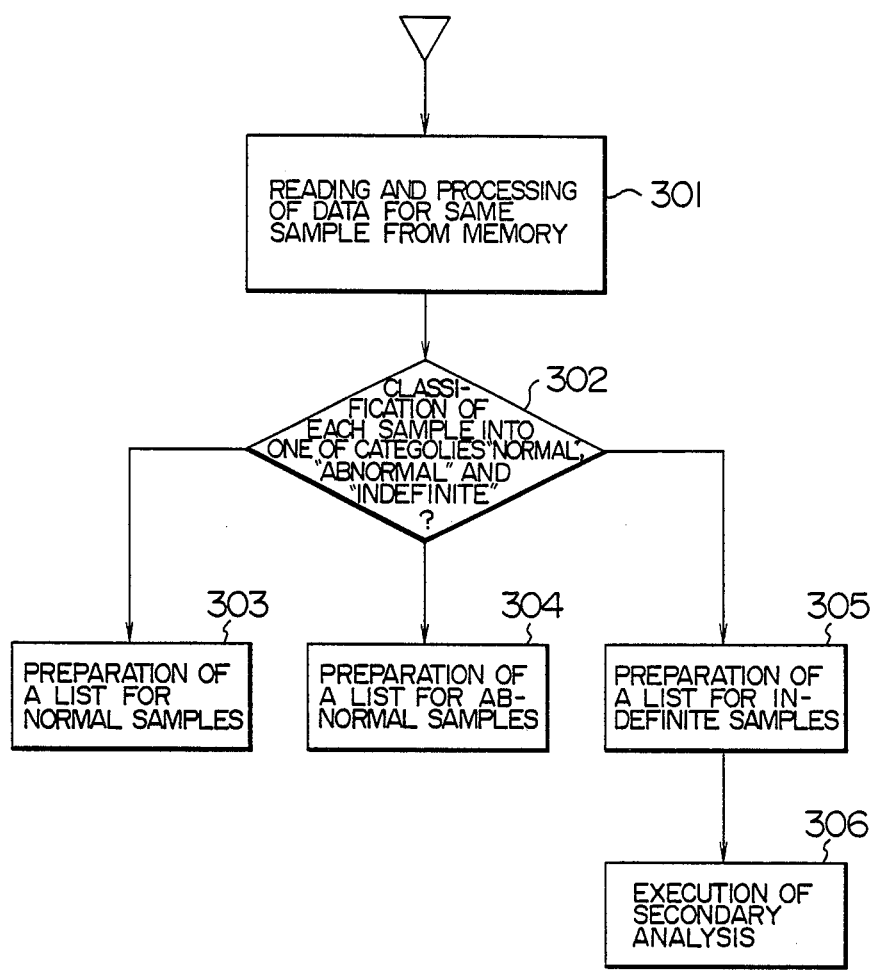

CELLULAR ANALYSIS SYSTEM

BACKGROUND OF THE INVENTION

The present invention generally relates to a cell analyzing apparatus. More particularly, the invention concerns a cellular analysis system suited for recognizing images of blood cells for discrimination of normal and abnormal cells from each other, classification of blood cells as well as counting thereof for the purpose of diagnostically determining blood diseases such as leukemia, anemia or the like.

In the hitherto known cellular analysis apparatus, the image of a blood cell is picked up by means of a microscope equipped with a television camera to derive chromatic density information of the blood cell image for thereby extracting the characteristic features such as cell area, peripheral length, nuclear area and others. On the basis of these extracted characteristic quantities, a relationship between the nuclear area on one hand and the ratio of the squared nuclear peripheral length to the nuclear area and the like are determined for recognition and classification of the blood cell under test.

Blood contains various components such as white blood cells, red blood cells, platelets and others. In conjunction with the detection and classification of the various blood cells, there are known various effective staining methods for the respective blood cells. The classification of the blood cells and discriminative identification of normal and abnormal cells by means of the cell analyzing apparatus are practiced after staining the blood cells by the respective effective staining methods. As the staining methods which are effective for the variety of blood cells, there are known those methods as mentioned below. For the classification of normal white blood cells (six species) and red blood cells (three species) as well as for the counting of platelets, May-Grünwald-Giemsa staining is adopted. On the other hand, for the counting of recticulocytes, a supravital staining method is employed. Further, for the detection of the abnormal white blood cells, i.e. blasts and immature cells which will appear in the case of leukemia, a peroxidase staining method is adopted.

In the hitherto known analytical examination of the blood cell images which have, a set of stained samples undergone the various stainings mentioned above are prepared, wherein the classification of the blood cells and discriminative determination as to the normal or abnormal cell are practiced for the individual stained samples, respectively. For example, after the classification of white blood cells based on the sample stained by the May-Grünwald-Giemsa method, the cell images of the sample stained supravitally are examined by changing the analyzing procedure. The same holds true also in the case of the sample stained by the peroxidase method.

Through the analyses of the blood cell images by using the variety of stained samples mentioned above, abnormal ratio among the six species of white blood cells, detection of abnormality indicated by the presence of immature cells and blasts, recognition of the normal blood cells, detection of indistinct or indefinite cells possibly produced by failure in the staining or physical injuries and others can be accomplished.

The sample which has proved to contain the abnormal and/or indefinite cells as the result of the analysis performed as mentioned above, are subjected to visual examination by a technician after mechanical retrieval to make a decision as to whether the sample indicates hemopathy (blood disease). In a hitherto known cellular analysis system exemplified by the one described in U.S. Pat. No. 3,851,972 issued on Dec. 3, 1974 and entitled "Automatic method and system for analysis and review of a plurality of stored slides", slides of samples prepared through a specific staining process undergo analysis of cells, whereby the slide in which an unidentifiable or abnormal cell has been found is memorized together with the position or location of the cell. After the whole analysis procedure has been completed, the slide in concern is retrieved and placed again in the microscope to review the unidentifiable cell through visual inspection. According to this known review system, a number of slides are at once automatically analyzed and subsequently a set of slides which are to be reviewed are subjected to visual inspection en bloc for the purpose of reducing the time required for the examination.

In connection with the hitherto known cell analyzing system, it should be mentioned that the number of cells analyzed automatically for a single sample is ordinarily about 100 per slide for one sample. This is because the time taken for the examination will become increased intolerably in case a greater number of cells are to be examined. In particular, in the inspection institutions such as hospitals where a large number of samples have to be handled, the number of cells to be analyzed is selected to be about 100 from the standpoint of efficiency to be realized in the examination.

In general, a major portion of the slides of samples to be examined in a hospital in a day, i.e. 90% or more of the samples picked from ordinary patients have proved to be essentially normal when inspected by a doctor or technician. However, even these normal samples each contain the unidentifiable cells in the ratio of 1 or 2 to 100 cells due to failure in the staining and/or physical injuries. Under the circumstances, 90% or more of the samples loaded in the cell analyzing apparatus require the visual inspection by a doctor, involving a lot of time and thus providing a great obstacle in enhancing the efficiency of the cellular analysis system.

Further, the hitherto known cell analysis system can scarcely ensure satisfactory statistical accuracy to the results of analysis because the number of cells to be automatically analyzed for one stained sample is generally about 100 per slide. Consequently, although no problem arises for clinical examinations in the case of a normal sample, there exists a possibility of abnormal cells being overlooked in the sample which was picked from a patient suffering hemopathy. Thus, the review through the visual inspection by a technician does not necessarily lead to the result of an examination which can assure a high reliability.

SUMMARY OF THE INVENTION

It is therefore an object of the present invention to provide a cellular analysis system which can assure an improved reliability in cellular examination while reducing labor involved therein.

In view of the above and other objects which will be more apparent as the description proceeds, the basic concept of the present invention lies in that a plurality of sample slides are prepared through different stainings, respectively, for one and the same sample for the purpose of comparatively examining the results of analyses for each of the individual sample slides to thereby derive the accurate decision even for the sample which cannot be examined with acceptable accuracy through the analysis of a single stained sample slide.

According to a general aspect of the present invention, there is provided a cellular analysis system for automatically analyzing sample slides prepared for a number of samples, including sample slide sets each being prepared through predetermined different staining processes which system comprises loading means for loading addressably and extractably the sample slides, image forming means for automatically picking out the sample slides in sequence from the setting means to feed the slide into the field of view of a microscope to thereby form an image of at least one cell contained in the sample slide observed through the microscope, feature extracting means for extracting morphological features of the cell image as digital information by analyzing the cell image formed by the image forming means, storage means for storing the digital information obtained through the feature extracting means together with a signal indicating an address of the associated sample slide in said loading means, and means for reading out the information derived from a set of the sample slides for each of the samples and stored in the storage means for thereby classifying the sample into one of plural predetermined categories on the basis of comprehensive judgment.

With the arrangement of the invention, information or data can be obtained simultaneously from a plurality of stained samples and can be collated simultaneously, whereby the number of samples to be visually reviewed can be decreased. As described hereinbefore, more than 90% of the ordinary samples which have undergone the blood cell examination are normal. Nevertheless, there exist blood cells having indefinite cellular images due to staining failure or injuries to the cells. In such case, visual review has heretofore been conducted on the sample containing these kind of cells. In contrast, the present invention teaches that a same sample be stained by different types of staining methods allows various data derived from the sample to be simultaneously collated with one another for thereby discriminatively identifying the indefinite or indistinct normal cells from the abnormal cells. As a consequence, the number of samples to be subjected to visual review because of inclusion of abnormal cells can be significantly decreased. Besides, since the secondary analysis which succeeds to the primary analysis can be conducted under more severe conditions (e.g. a larger number of cells are to be analyzed), the statistical error contained in the data resulting from the examination can be reduced to thereby enhance the reliability of data.

BRIEF DESCRIPTION OF THE DRAWINGS

FIG. 3 is a view for illustrating in a flow chart a procedure for making decision on the results of analysis made by the cellular analysis system according to the present invention.

DESCRIPTION OF THE PREFERRED EMBODIMENTS

Now, the invention will be described in detail in conjunction with an exemplary embodiment of the cellular analysis system with reference to the accompanying drawings on the assumption that the cellular analysis system is applied to automatic analysis of blood cells in a hospital.

Figure 1:
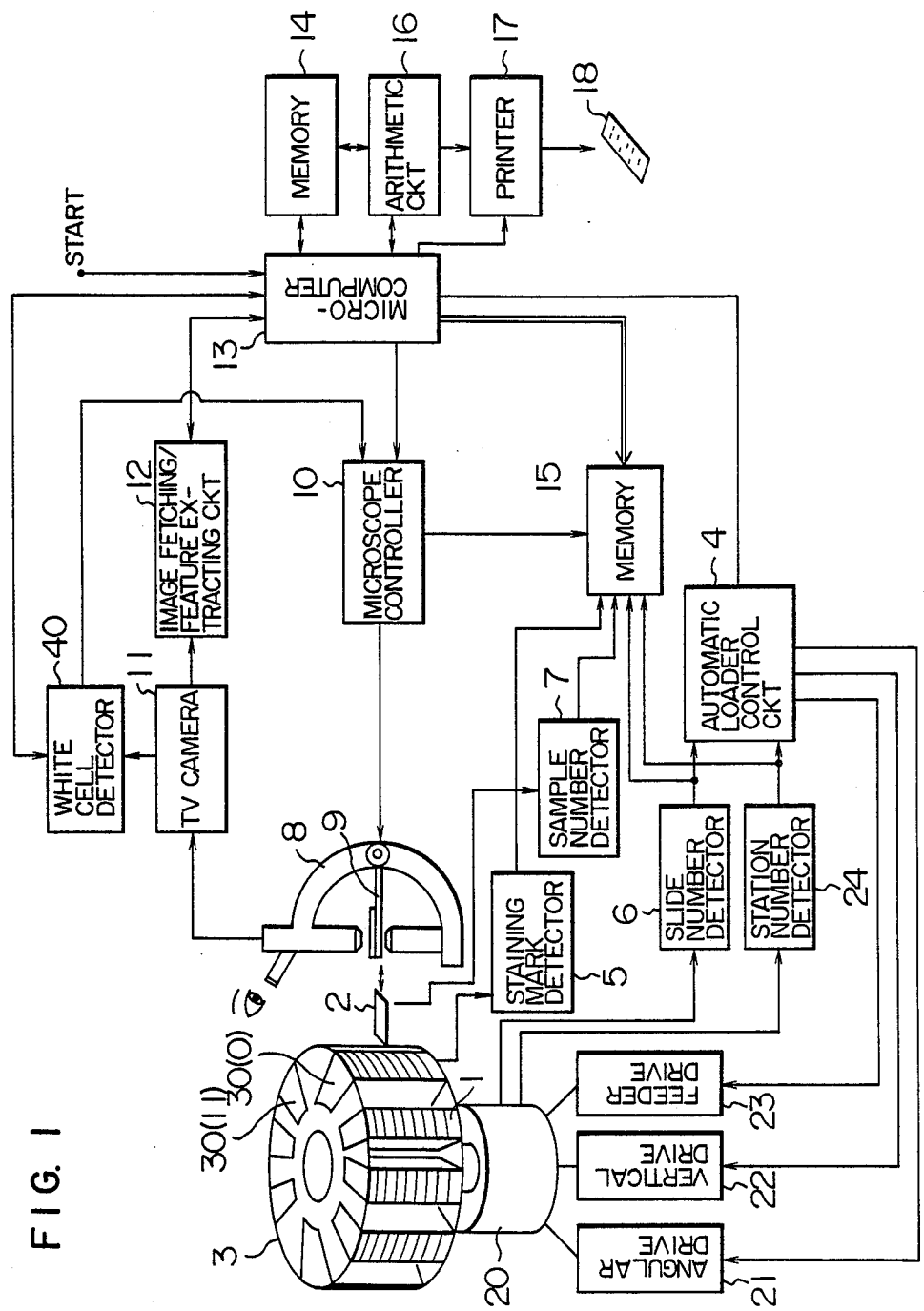
FIG. 1 is a view showing in a block diagram a general arrangement of a cellular analysis system according to an exemplary embodiment of the present invention.

Each of numerous blood samples to be analyzed is processed through predetermined different staining processes and sandwiched between two glass plates so as to be observed by a microscope, whereby a corresponding number of stained sample slides are prepared. These sample slides are classified with reference to the staining methods as adopted, and the slides of different samples, but prepared through the same staining process are placed in a same cassette 1. One cassette 1 may contain, for example, 25 sheets of slides. Accordingly, assuming that the number of samples to be analyzed is 100 and that each sample is treated through three different staining processes, 100 sheets of sample slides are prepared by each staining method, which means that the total number of the sample slides amounts to 300, whereby 12 cassettes each containing 25 sample slides prepared through the identical staining process are provided. These cassettes 1 are set or placed in a sample automatic loader 3 at a plurality of cassette stations generally denoted by 30($n$) (where n represents the station identifying number), as shown in FIG. 1. The sample automatic loader 3 is equipped with a drive mechanism 20 which is constituted by an angular or rotational driving apparatus 21 for rotating the automatic loader in the counter clockwise direction, a vertical driving apparatus 22 for driving vertically the automatic loader and a feeder driving apparatus 23 for operating a cassette feeder in such a manner that one sample slide is taken out from a cassette located at a predetermined transfer position to be thereby moved onto a X-Y stage of a microscope 8 while after observation the slide is restored in the cassette at the original position. The various driving apparatus mentioned above can be operated independent of one another under the control of an automatic loader control circuit 4. Since such automatic loader mechanism itself is known, further description thereof will be unnecessary.

Each cassette is labelled with a mark indicating the staining process which the sample slides contained therein have undergone, while each sample slide is attached with a sample identification number allowing the identification of the sample contained in the slide. The staining indication mark and the sample identification mark or number are detected by a staining indication mark detector 5 and a sample identification number detector 7, respectively, the results of detection being stored in a memory 15. A microcomputer 13 for controlling operations of the cellular analysis system is provided with a memory (ROM) 14 storing programs for controlling operations of the automatic loader 3, the X-Y stage 9 and a printer 17 in accordance with analyzing procedure empirically determined by physician for each of the staining processes and for each of primary and secondary analyzing procedures. The contents of the programs will be elucidated hereinafter.

It is now assumed that the automatic loader 3 is located such that one of the cassette stations, e.g. the station 30(0) is disposed at an angular position opposite to the sample slide pick-out position and at the top limit within the range of its vertical movement so that the feeder mechanism can pick out the lowermost one of the sample slides from the cassette placed at the cassette station 30(0). Upon activation of the automatic loader control circuit 4 by the microcomputer 13, a trigger signal is applied to the feeder drive control circuit 23, whereby the sample slide 2 located at the lowermost position within the cassette set at the station 30(0) is transferred onto the X-Y stage of the microscope 8. At that time, the identification number of the cassette station located at the sample pick-out position, e.g. the number (0), is read by the station number detector 24, while the identification number of the sample slide being picked out is detected by the slide number detector 6, the resulting signals representative of the detected identification numbers being stored in the memory 15 and also fed back to the automatic loader control circuit 4 to be utilized for controlling the angular and vertical positions of the automatic loader 3. Further, during the transfer of the sample slide to the X-Y stage, the sample identification number attached to the slide is detected by the sample identification number detector 7 to be subsequently stored in the memory 15. In this connection, it should be mentioned that the station identification number can be detected by any conventional detecting means on the basis of correspondence between the angular position of the automatic loader driven by the rotational driving apparatus and the cassette station. Further, in connection with the detection of the slide identification number, serial numbers (e.g. 0 to 24) may be allocated to all the slides in the order from the lowermost one to the uppermost one in each of the cassettes, wherein the slide identification number may be detected on the basis of correspondence relation between the vertical position of the automatic loader 3 driven by the vertical driving apparatus and the slide located at the pick-out position. To this end, any suitable detecting means known per se may be employed.

The X-Y stage is coupled to a microscope controller 10 serving for adjustment of the stage of the microscope, adjustment of focal point, lubrication and other functions. A television camera 11 is connected to a lens column of the microscope 8. The television camera 11 has the output connected to an image data fetching/feature extracting circuit 12 for fetching the cellular image in terms of digital image resulting from analogue-to-digital A/D conversion processing and for extracting morphological features of the cell. Since the structure of the image fetching/feature extracting circuit 12 itself is known, further description will be unnecessary. Connected to the image fetching/feature extracting circuit 12 is a computer controller (microcomputer) 13 which serves for discrimination and classification of cells and a system control. The computer controller 13 in turn is connected to the memory 14 for storing data resulting from analysis and the various programs mentioned hereinbefore and an arithmetic circuit 16 serving for collation and arithmetic processing of the data. It will be noted that the memory 14 and the arithmetic circuit 16 are also connected to each other. Further, the arithmetic circuit 16 is connected to the printer 17 for printing out the result of analysis. Through the printer 17, a report sheet recording the results of analysis is made available.

Next referring to a flow chart shown in FIG. 2A, operation of the system will be described. Upon application of a start signal to the microcomputer 13, the whole system is set to the state ready for operation, while the microcomputer 13 is initialized (step 100). More specifically, assuming, for example, that examination or inspection is to be carried out starting from the sample slide located at the lowermost shelf of the cassette station No. (0), the initialization mentioned above causes both the cassette number n and the slide number m assigned to predetermined areas of the memory 14 to be reset to "0". Subsequently, the automatic loader control circuit 4 is activated to supply drive signals to the angular driving apparatus 21 and the vertical driving apparatus 22, respectively, as the result of which the automatic loader 3 is driven angularly and vertically to a position aligned with the position where the slide identified by the number m="0" (the lowermost slide) within the cassette of the identification number n="0" at the station No. (0) can be picked out (step 101). Next, the feeder driving apparatus 23 is activated to pick out the sample slide located at the pick-out position to be subsequently placed on the X-Y stage of the microscope (step 102). Thereafter, the output signals of the slide number detector 6, the station number detector 24, the staining identification mark detector 5 and the sample identification number detector 7 stored in the memory 15 are read out (step 103) to identify the type of the staining through which the sample of the cassette under consideration has been processed on the basis of the signal of the staining identification mark detector (step 104), being followed by selection of the program stored in the memory 14, corresponding to the analysis procedure determined previously for the primary analysis of the sample slide of the identified staining (step 105), whereby the primary analysis is performed in accordance with the selected program (step 106). Concerning details of this step 106, description will be made hereinafter with reference to FIG. 2B. After the processing at the step 106 has been completed, the procedure proceeds to a step 107 where the slide identification number m is added with "1", being followed by a step 108 where it is decided whether m is equal to or greater than the number of the slides contained in one cassette (25 in the case of the illustrated embodiment). If the answer of the decision step 108 is affirmative, the procedure proceeds to a step 109. Otherwise, the step 101 is regained to perform the primary analysis for the next sample slide in the same cassette. On the other hand, at the step 109, the slide identification number m is set to "0", while the cassette identification number n is added with "1", being followed by a step 110 where the incremented cassette identification number n is compared with the number of the cassette station (i.e. 12 in the case of the illustrated embodiment). If n is equal to or greater than 12, the procedure proceeds to a step 111. Otherwise, the step 101 is regained to perform the primary analysis for the lowermost sample slide of the next cassette. When n=12 at the step 110, this means that the primary analysis has been completed for all the sample slides accommodated in the automatic loader. Accordingly, n is reset to "0" at the step 111 which is followed by a step 112 where the results of the analysis performed until then are loaded into the memory 14 and put in order. Concerning the details of the step 112, description will be made hereinafter by referring to FIG. 3.

Now, description will be made on the processing executed at the step 106. This processing is executed in accordance with a program selected in accordance with the type of staining method. As mentioned hereinbefore, as the staining methods employed in the examination of blood cells, there are available ordinary staining methods employed for identification of six species of normal white blood cells and three species of normal red blood cells as well as for the counting of platelets as exemplified by May-Grünwald-Giemsa staining, a supravital staining method employed for the counting of reticulocytes as exemplified by new methylene blue staining, and a specific staining method employed for examination of hemopathy such as leukemia or abnormal white blood cells, as exemplified by peroxidase staining. In this connection, it should be noted that the procedures for examining or inspecting the slides of samples processed by these staining methods differ in dependence on the staining methods and that examination procedure of the sample processed by the same staining method differs between the primary and the secondary analyses. The following description made with reference to FIG. 2B is directed to the processing involved in conducting the primary analysis of white blood cells for the sample stained by the May-Grünwald-Giemsa staining, a typical one of the ordinary staining methods.

At first, a microscope controller 10 is activated in response to a signal 13 issued by the microcomputer 13. Under the control of the controller 10, the X-Y stage of the microscope is so driven that the field of view of the microscope 8 scans the sample slide along a predetermined path (step 201). The path for the scanning is empirically determined by the physician. The field of view of the microscope 8 is observed by the television camera 11 to monitor whether image of white blood cell is visible within the field of view by means of a white blood cell monitor 40 (step 202). Upon detection of the white blood cell, the detector 40 produces a signal for stopping the scanning operation of the X-Y stage through the microscope controller 10 (step 203). The microcomputer 13 also responds to the reception of this detection signal for activating the image fetching/feature extracting circuit 12 for measuring physical quantities concerning the morphological features of the white blood cell image, the measured quantities being converted into digital signals to be subsequently supplied to the computer 13 (step 204). Upon completion of the measurement, the sample slide is returned to the automatic loader (step 205). The program then proceeds to a step 206 where the number p of detected white blood cells (this number is initially equal to "0") is added with "1", being followed by a step 207 where it is decided whether the number (times) of white blood cell examinations (p+1) has attained a preset number of white blood cells, e.g. "100". If not, the step 201 is regained to start again the scanning operation of the X-Y stage 9 of the microscope 8. In the meanwhile, the computer 13 arithmetically determines the morphological features of the cell by means of the arithmetic unit 16 on the basis of the physical quantities received from the image fetching/feature extracting circuit 12 for performing classification and identification of the white blood cell, the results of which are then stored in the memory 14 together with the sample identification number, the cassette number and the slide number.

On the other hand, when the number (times) of examinations has attained "100" at the step 207, the procedure proceeds to a step 208 where data obtained till then are put in order, and the step 107 is regained (step 209). Under the command derived from the step 207, the computer 13 waits for completion of the arithmetic processing of the last white blood cell image and puts in order all the results of the arithmetic operations for the same sample slide to be subsequently stored in the memory 14. The morphological characteristic quantities of a white blood any cell (or cell in general) may be represented by a number of physical quantities such as, for example, area of the cell, unclear area, peripheral length of the cell, degrees of light absorption of specific wavelengths by cells, nuclei and the like. These quantities are arithmetically determined at high speeds and comparatively processed with reference to the cell identification standards programmed and stored in the memory 14, whereby the cells as found are identified and classified into predetermined varieties of the known cells, such as lymphocyte, eosinophil, basophil, neutrophil, monocyte,—etc. This analysis includes detection of six species of white blood cells and others as well as the counting of reticulocytes. When a blood cell under test is found unable to be classified into any categories of the known cells with the aid of the cell identification program, the cell under test is then classified into a category of unidentifiable cells. The analytical procedures for the individual cells can be empirically determined by the physician. Further, since the image fetching/feature extracting circuit is within knowledge of those skilled in the art, any further description thereof will be unnecessary.

As will be appreciated from the above description, the memory 14 stores therein the results of analyses of 100 white blood cells put in order together with the sample identification number attached to the associated sample slide, the slide identification number and the cassette identification number at the level where the analyses for one sample slide comes to an end. As described hereinbefore, decision as to whether a sample under test is normal or abnormal has heretofore been made on the basis of the results of analysis of the sample slide prepared by one staining method. However, the samples which are difficult to be identified with only the data obtained from the sample slide prepared by one staining method amount to a considerable number, and the technician is forced to visually examine again these samples, which requires very time-consuming labor. In contrast, according to the teachings of the present invention, a plurality of sample slides prepared for one sample through a plurality of different staining methods, respectively, are provided and analyzed through the process described above in conjunction with FIG. 2A, whereby at the stage succeeding to the final step 111, the results of analyses performed for a plurality of sample slides prepared for one sample (e.g. three sample slides prepared through different stainings) can be obtained and stored in the memory 14. The data thus obtained is then subjected to a comprehensive decision or judgment at a step 112. Now, description will be made of the processing executed at the step 112 by referring to FIG. 3.

At first, the data stored in the memory are orderly rearranged for each of the samples (step 301). Assuming that three sample slides have been prepared for each sample by the different staining methods, respectively, the data derived from the three sample slides for each sample are collected and stored in the memory in order. Next, on the basis of the rearranged data for each sample, a decision is made as to which one of predetermined categories i.e. normal, abnormal and indefinite (unidentifiable) that sample is to be classified at a step 302 in accordance with predetermined rules which may be empirically determined by the technician and stored in the memory 14. Upon completion of the decision for all the samples, there are prepared lists of the normal samples, abnormal samples and indefinite samples (steps 303, 304 and 305, respectively). Each of these lists contains the slide identification numbers of the sample slides used for each sample (three sample slides in the case of the illustrated embodiment), the cassette identification number and the measurement data. These lists can be printed out by the printer 17 as occasion requires. For the sample which is indefinite, the secondary analysis is performed at a step 306.

Figure 2A:
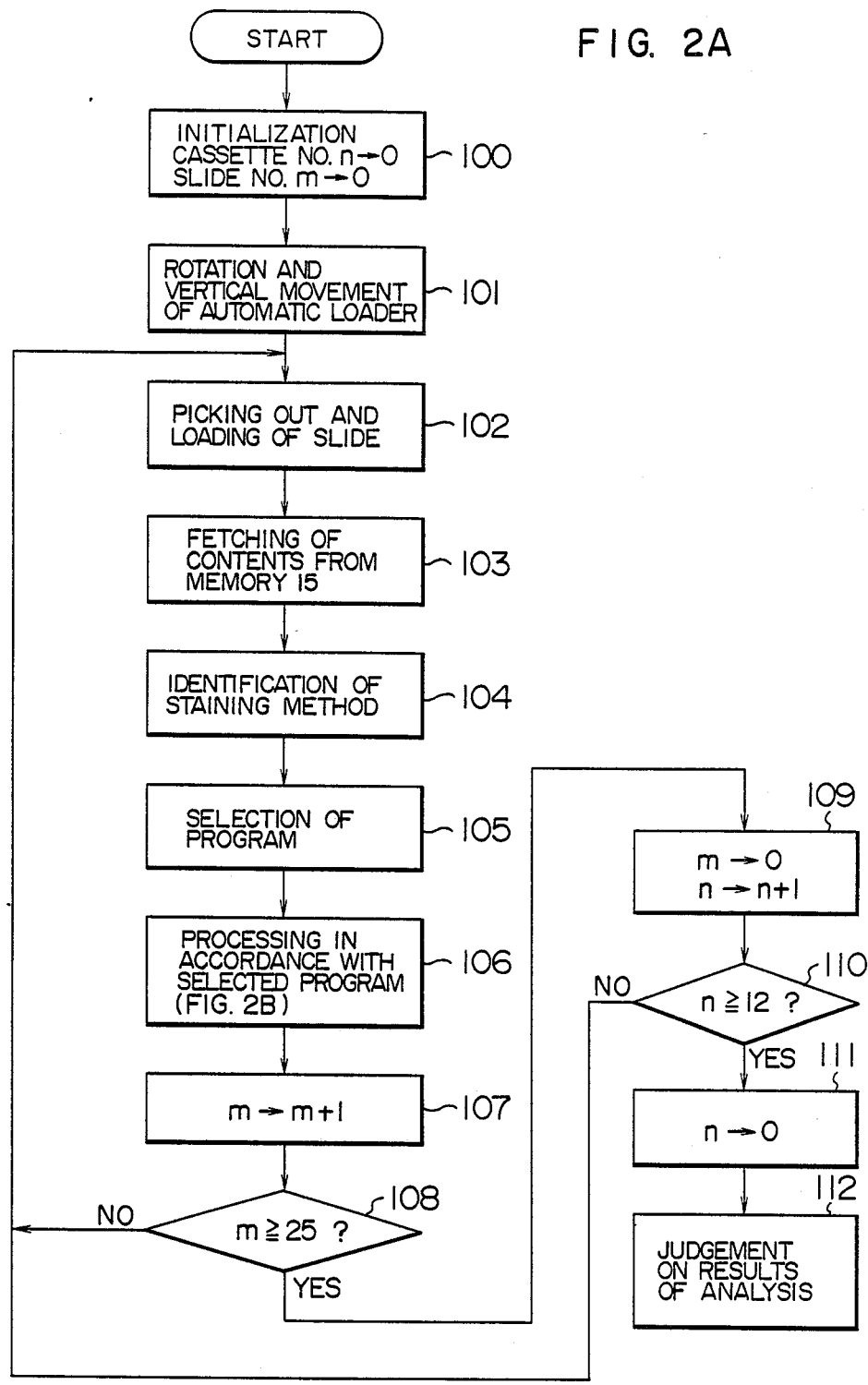
FIGS. 2A and 2B are views for illustrating in flow charts processing operations of the cellular analysis system according to the invention.
Figure 2B:
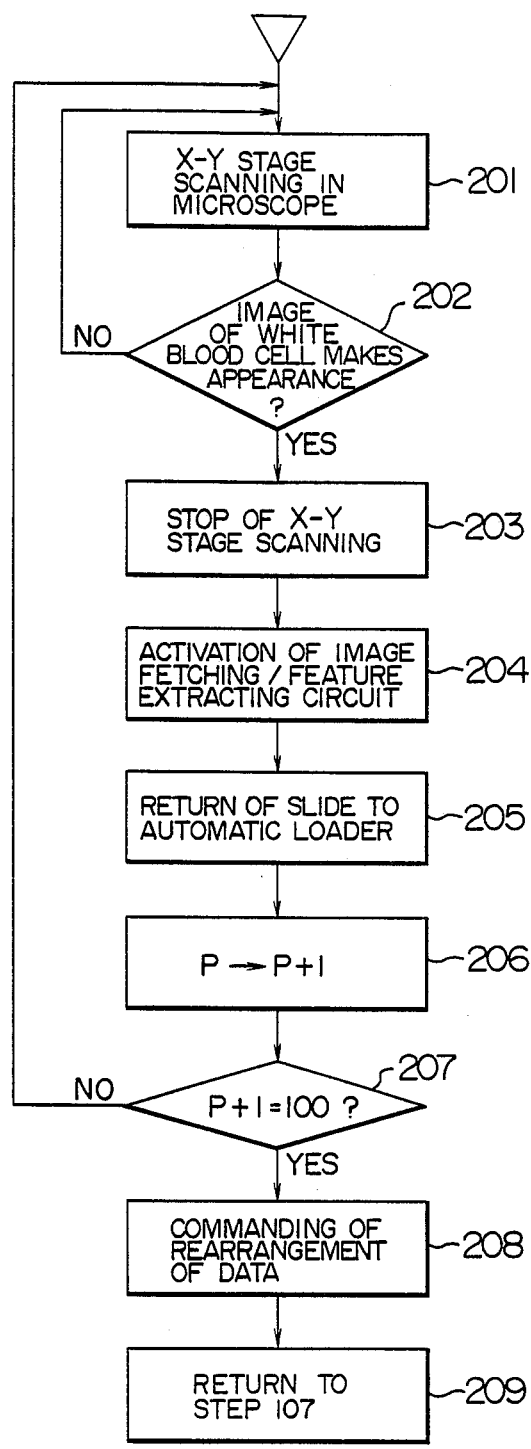

Basically, the secondary analysis is conducted in accordance with similar processes to those illustrated in FIGS. 2A and 2B. Difference resides simply in that the program is so prepared that only the sample slides listed up at the step 305 are examined and that a program for the secondary examination is selected at a step 105. The program for the secondary analysis is so prepared that more precise or accurate measurements can be accomplished when compared with the program for the primary analysis. In the primary analysis, the morphological characteristics of a predetermined number of cells such as white blood cells are measured by scanning the sample slide in the microscope, wherein the results of measurements obtained for the individual cells are compared with the preestablished standards for classification and identification to thereby determine which categories the cells in concern belong to. At the level where the analyses for 100 white blood cells have been completed, decision is made as to the normality or abnormality or indefiniteness in dependence on the proportion by percent of the cells classified into the abnormal cell category. However, the scanning in the primary analysis is restricted to an extremely small portion of the sample slide. Besides, abnormal cells may be locally maldistributed in dependence on the preparation method of the sample slides. Under the circumstances, in the secondary analysis, the scanning by the X-Y stage in the microscope may be preferably performed along the path which differs from the scanning path taken in the primary analysis and/or the number of cells to be measured for one slide may be increased when compared with that of the primary analysis to thereby enhance the accuracy of the measurement. The results of the secondary analysis thus obtained are judged synthetically with those of the primary analysis to determine the normality or abnormality of the sample in concern. This decision is also made in accordance with a decision program prepared in consideration of the rules empirically established by the technician. It goes without saying that the sample determined to be abnormal through the primary analysis can be readily subjected to the secondary analysis with the system according to the invention, when the physician considers it necessary.

We claim:

1. A cellular analysis system for automatically analyzing sample slides prepared for a number of samples, including sample slide sets each being prepared through predetermined different staining processes, comprising:
   loading means for loading addressably and extractably said sample slides;
   image forming means for automatically picking out said sample slides in sequence from said loading means to feed said slides into the field of view of a microscope to thereby form an image of at least one cell contained in said sample slide under observation of said microscope;
   feature extracting means for extracting morphological features of said cell image as digital information by analyzing said cell image formed by said image forming means;
   storage means for storing said digital information obtained through said feature extracting means together with a signal indicating an address of the associated sample slide in said loading means;
   means for reading out said information derived from a set of the sample slides for each of the samples and stored in the storage means for thereby classifying said sample into one of plural predetermined categories on the basis of a comprehensive determination, wherein one of said categories indicates necessity for more accurate analysis, said sample slides associated with said samples being classified into said one of said categories being subjected to a secondary analysis, and wherein in said secondary analysis, said feature extracting means performs analysis for a greater number of cells than that of the cells analyzed in the primary analysis.

2. A cellular analysis system for automatically analyzing sample slides which are prepared by staining said samples using predetermined different staining processes and which are provided with staining marks indicative of the staining processes by which the samples of the slides are stained respectively, said system comprising:
   loading means for loading addressably and extractably said sample slides;
   memory means for preliminarily storing programs of analyzing procedures prepared for said respective staining processes;
   means for transporting said sample slides successively from said loading means into a microscopic observation stage;
   means for detecting said staining marks provided on said sample slides;
   means responsive to the detection of said staining mark on each sample slide for selecting one of said programs stored in said memory means corresponding to said staining process indicated by said detected staining mark; and
   means for applying a primary microscopic observation and analysis of the sample slide transported onto said microscopic stage according to said selected program, including means for forming an image of at least one cell contained on said sample slide under observation of a microscopic and feature extracting means for extracting morphological features of said image as digital information by analyzing said cell image according to said selected program.

3. A cellular analysis system according to claim 2, wherein each of said sample slides is marked by a sample code for identification of the particular sample on each sample slide, said system further comprising:
   means for detecting said sample code marked on each of said sample slides;
   storage means for storing said digital information obtained from each of said sample slides together with said detected sample code of each of said sample slides;
   means for reading out of said storage means all said digital information stored therein together with said sample code for each corresponding one of said samples; and
   means for determining abnormalities of each sample based on said read-out digital information according to a predetermined rule.

4. A cellular analysis system according to claim 3, wherein said determining means includes means for classifying each sample into one of the categories normal, abnormal and indefinite based on the results of said determination, said system further comprising means for applying a secondary analysis to said sample slides when a sample is classified into the indefinite category.

5. A cellular analysis system according to claim 4, wherein said primary analysis includes an analysis of a predetermined first number of cells contained in each sample slide and said secondary analysis includes a analysis of a predetermined second number of cells contained in each sample slide, said second number being larger than said first number.

6. A cellular analysis system according to claim 2, wherein said loading means includes cassettes for loading addressably and extractably only sample slides prepared by the same staining process, said staining mark indicating said staining process for said sample slides contained in each cassette being recorded on each corresponding cassette so as to be detectable by said staining mark detecting means.

* * * * *